(12) United States Patent
Watakabe

(10) Patent No.: US 11,518,832 B2
(45) Date of Patent: Dec. 6, 2022

(54) FLUORINE-CONTAINING DIENE COMPOUND, FLUORINE-CONTAINING POLYMER, AND METHODS FOR PRODUCING SAME

(71) Applicant: AGC Inc., Tokyo (JP)

(72) Inventor: Atsushi Watakabe, Tokyo (JP)

(73) Assignee: AGC Inc., Tokyo (JP)

( * ) Notice: Subject to any disclaimer, the term of this patent is extended or adjusted under 35 U.S.C. 154(b) by 173 days.

(21) Appl. No.: 16/908,872

(22) Filed: Jun. 23, 2020

(65) Prior Publication Data

US 2020/0317834 A1    Oct. 8, 2020

Related U.S. Application Data

(63) Continuation-in-part of application No. PCT/JP2018/047662, filed on Dec. 25, 2018.

(30) Foreign Application Priority Data

Dec. 26, 2017 (JP) .............................. JP2017-249732

(51) Int. Cl.
  *C08F 2/06* (2006.01)
  *C08F 236/20* (2006.01)
  *C08F 214/20* (2006.01)

(52) U.S. Cl.
  CPC .............. *C08F 214/20* (2013.01); *C08F 2/06* (2013.01); *C08F 236/20* (2013.01)

(58) Field of Classification Search
  CPC .............................. C08F 214/20; C08F 236/20
  See application file for complete search history.

(56) References Cited

U.S. PATENT DOCUMENTS

2015/0243856 A1    8/2015    Yamada et al.

FOREIGN PATENT DOCUMENTS

| JP | 63-48314 A1 | 3/1988 |
| WO | WO 2005/095471 A1 | 10/2005 |
| WO | WO 2009/036131 A2 | 3/2009 |
| WO | WO 2010/147815 A2 | 12/2010 |
| WO | WO 2014/178288 A1 | 11/2014 |
| WO | WO 2018/118956 A | 6/2018 |
| WO | WO 2018/136331 A1 | 7/2018 |

OTHER PUBLICATIONS

International Search Report dated Apr. 2, 2019, in PCT/JP2018/047662 (PCT/ISA/210) (5 pages, with English Translation).
International Search Report dated Apr. 2, 2019, in PCT/JP2018/047662 (PCT/ISA/237) (4 pages).
Molecules 2011, 16, 6512-6540.
Extended European Search Report dated Oct. 5, 2021 in European Patent Application No. 18893378.2, 5 pages.

*Primary Examiner* — Catherine S Branch
(74) *Attorney, Agent, or Firm* — Oblon, McClelland, Maier & Neustadt, L.L.P.

(57) ABSTRACT

The present invention relates to a fluorine-containing diene compound represented by the following formula I, and to a polymer thereof. In the formula, each of $R^1$ to $R^7$ is independently a hydrogen atom, a chlorine atom, a fluorine atom, or an alkyl group having a carbon number of 1 to 5 which may be substituted by a fluorine atom, k is 0 or 1, and at least one of $R^1$ to $R^7$ is a hydrogen atom.

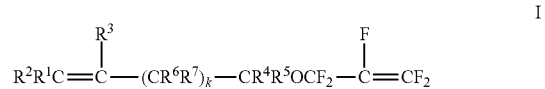

I

12 Claims, No Drawings

FLUORINE-CONTAINING DIENE COMPOUND, FLUORINE-CONTAINING POLYMER, AND METHODS FOR PRODUCING SAME

TECHNICAL FIELD

The present invention relates to a novel fluorine-containing diene compound, more specifically, a diene compound containing a fluorine atom, a fluorine-containing polymer, and production methods thereof.

BACKGROUND ART

A polymer containing a fluorine atom in the main chain and obtained from a fluorine-containing unsaturated compound as a raw material monomer has an excellent balance of various properties such as low refractive index, low dielectric constant, water repellency/oil repellency, heat resistance, chemical resistance, chemical stability and transparency and is used in a wide variety of fields such as electric/electronic materials, semiconductor materials, optical materials and surface-treating agents.

Among others, in the case where a fluorine-containing compound as a raw material monomer is a fluorine-containing diene compound having two carbon-carbon double bonds and having a total number of carbon atoms and oxygen atoms intervening between the carbon-carbon double bonds of 2 or 3 (carbon atoms constituting the carbon-carbon double bonds are not counted; in the case of having a branched (branching) structure, carbon atoms and oxygen atoms contained in the branch are not counted), cyclopolymerization is possible and a polymer having a 5-membered or 6-membered ring structure in the main chain is primarily produced. Such a fluorine-containing diene compound has heretofore been usually synthesized in multiple steps.

Non-Patent Literature 1 states that perfluoroallyl fluorosulfate ($CF_2=CFCF_2OSO_2F$) is obtained from hexafluoropropene ($CF_2=CFCF_3$) in one step. It is reported that various compounds can be synthesized from the perfluoroallyl fluorosulfate.

CITATION LIST

Non-Patent Literature

Non-Patent Literature 1: Molecules 2011, 16, 6512-6540

SUMMARY OF INVENTION

Technical Problem

However, in conventional technology including Non-Patent Literature 1, there is no report that a partially fluorinated diene compound was synthesized from perfluoroallyl fluorosulfate.

Accordingly, an object of the present invention is to provide a novel diene compound containing a fluorine atom (fluorine-containing diene compound) which can be synthesized in a small number of steps, and a novel fluorine-containing polymer using the fluorine-containing diene compound as a raw material monomer. It is also an object to provide production methods of these.

Solution to Problem

As the configurations for achieving the objects above, the present invention relates to the following <1> to <12>.

<1> A fluorine-containing diene compound represented by the following formula I:

[Chem. 1]

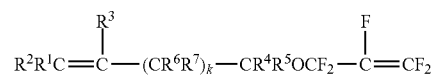

In the formula, each of $R^1$ to $R^7$ is independently a hydrogen atom, a chlorine atom, a fluorine atom, or an alkyl group having a carbon number of 1 to 5 which may be substituted by a fluorine atom, k is 0 or 1, and at least one of $R^1$ to $R^7$ is a hydrogen atom.

<2> The fluorine-containing diene compound according to <1> above, wherein in formula I, each of $R^1$ and $R^2$ is independently a hydrogen atom or a fluorine atom, $R^3$ is a hydrogen atom, a chlorine atom, a fluorine atom, a methyl group, or a trifluoromethyl group, and each of $R^4$ and $R^5$ is independently a hydrogen atom, a methyl group, or a trifluoromethyl group.

<3> A method for producing a fluorine-containing diene compound represented by the following formula I, including reacting a compound represented by the following formula a with a compound represented by the following formula b in the presence of a base.

[Chem. 2]

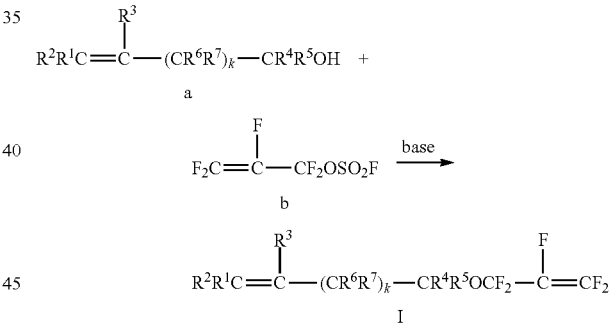

In the formulae, each of $R^1$ to $R^7$ is independently a hydrogen atom, a chlorine atom, a fluorine atom, or an alkyl group having a carbon number of 1 to 5 which may be substituted by a fluorine atom, k is 0 or 1, and at least one of $R^1$ to $R^7$ is a hydrogen atom.

<4> The method for producing a fluorine-containing diene compound according to <3> above, wherein the reaction is performed in the presence of a solvent.

<5> The method for producing a fluorine-containing diene compound according to <3> or <4> above, wherein the base is an aliphatic tertiary amine.

<6> The method for producing a fluorine-containing diene compound according to <4> or <5> above, wherein the solvent contains at least either one of glyme and nitrile.

<7> A fluorine-containing polymer obtained from a fluorine-containing compound represented by the following formula I' as a raw material monomer.

[Chem. 3]

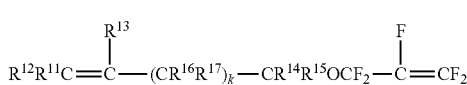

I'

In the formula, each of $R^{11}$ to $R^{17}$ is independently a hydrogen atom, a chlorine atom, a fluorine atom, or a monovalent organic group which may have a heteroatom, k is 0 or 1, at least one of $R^{11}$ to $R^{17}$ is a hydrogen atom, $R^{11}$ or $R^{12}$ may combine with any one of $R^{13}$ to $R^{17}$ to form a ring, and $R^{13}$ may combine with any one of $R^{11}$, $R^{12}$ and $R^{14}$ to $R^{17}$ to form a ring.

<8> The fluorine-containing polymer according to <7> above, wherein the fluorine-containing compound represented by the formula I' is a fluorine-containing diene compound represented by the following formula I.

[Chem. 4]

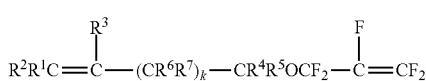

I

In the formula, each of $R^1$ to $R^7$ is independently a hydrogen atom, a chlorine atom, a fluorine atom, or an alkyl group having a carbon number of 1 to 5 which may be substituted by a fluorine atom, k is 0 or 1, and at least one of $R^1$ to $R^7$ is a hydrogen atom.

<9> The fluorine-containing polymer according to <8> above, wherein in formula I, each of $R^1$ and $R^2$ is independently a hydrogen atom or a fluorine atom, $R^3$ is a hydrogen atom, a chlorine atom, a fluorine atom, a methyl group, or a trifluoromethyl group, and each of $R^4$ and $R^5$ is independently a hydrogen atom, a methyl group, or a trifluoromethyl group.

<10> A method for producing a fluorine-containing polymer, including a step of polymerizing a raw material monomer containing a fluorine-containing compound represented by the following formula I'.

[Chem. 5]

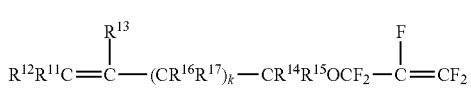

I'

In the formula, each of $R^{11}$ to $R^{17}$ is independently a hydrogen atom, a chlorine atom, a fluorine atom, or a monovalent organic group which may have a heteroatom, k is 0 or 1, at least one of $R^{11}$ to $R^{17}$ is a hydrogen atom, $R^{11}$ or $R^{12}$ may combine with any one of $R^{13}$ to $R^{17}$ to form a ring, and $R^{13}$ may combine with any one of $R^{11}$, $R^{12}$ and $R^{14}$ to $R^{17}$ to form a ring.

<11> The method for producing a fluorine-containing polymer according to <10> above, wherein the fluorine-containing compound represented by formula I' is a fluorine-containing diene compound represented by the following formula I.

[Chem. 6]

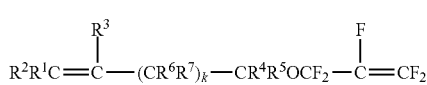

I

In the formula, each of $R^1$ to $R^7$ is independently a hydrogen atom, a chlorine atom, a fluorine atom, or an alkyl group having a carbon number of 1 to 5 which may be substituted by a fluorine atom, k is 0 or 1, and at least one of $R^1$ to $R^7$ is a hydrogen atom.

<12> The method for producing a fluorine-containing polymer according to <11> above, wherein in formula I, each of $R^1$ and $R^2$ is independently a hydrogen atom or a fluorine atom, $R^3$ is a hydrogen atom, a chlorine atom, a fluorine atom, a methyl group, or a trifluoromethyl group, and each of $R^4$ and $R^5$ is independently a hydrogen atom, a methyl group, or a trifluoromethyl group.

Advantageous Effects of Invention

In the present invention, a novel fluorine-containing diene compound is provided. A novel fluorine-containing polymer obtained from a fluorine-containing compound such as the fluorine-containing diene compound above as a raw material monomer is excellent in chemical durability, weather resistance, light transmissivity, transparency and liquid repellency and expected to offer a low dielectric constant. Therefore, the fluorine-containing polymer is anticipated to be utilized as an optical material, an electronic material, a surface-treating agent, etc.

Furthermore, a low-cost efficient production method capable of synthesizing the above-described useful fluorine-containing diene compound in a small number of steps is provided.

Description of Embodiments

The present invention is described in detail below, but the present invention is not limited to the following embodiments and can be implemented by arbitrarily making a modification without departing from the gist of the invention.

In the present description, a perfluoroalkyl group means a group in which all hydrogen atoms of an alkyl group are substituted by fluorine atoms. A (per)fluoroalkyl group is used as a collective term for a fluoroalkyl group and a perfluoroalkyl group. That is, the group is an alkyl group having one or more fluorine atoms.

<Fluorine-Containing Diene Compound>

The fluorine-containing diene compound of the present invention is a fluorine-containing diene compound represented by the formula I.

In the formula I, each of $R^1$ to $R^7$ is independently a hydrogen atom, a chlorine atom, a fluorine atom, or an alkyl group having a carbon number of 1 to 5 which may be substituted by a fluorine atom, k is 0 or 1, and at least one of $R^1$ to $R^7$ is a hydrogen atom.

In the formula I, since at least one of $R^1$ to $R^7$ is a hydrogen atom, the fluorine-containing diene compound of the present invention is a partially fluorinated compound and is not a perfluoro compound.

Out of $R^1$ to $R^7$, each of $R^1$ and $R^2$ is independently, preferably a hydrogen atom, a fluorine atom, a methyl group, or a trifluoromethyl group, because the polymerization reactivity of the fluorine-containing diene compound increases, and is more preferably a hydrogen atom or a fluorine atom.

$R^3$ is preferably a hydrogen atom, a chlorine atom, a fluorine atom, a methyl group, or a trifluoromethyl group, because the polymerization reactivity of the fluorine-containing diene compound increases.

Each of $R^4$ and $R^5$ is independently, preferably a hydrogen atom, a methyl group, or a trifluoromethyl group, because the compound (compound a) represented by the later-described formula (a) is made stable. In the case where $R^4$ or $R^5$ is a fluorine atom, elimination of hydrogen fluoride (HF) readily occurs and consequently, the structure is likely to be unstable.

Each of $R^6$ and $R^7$ is independently, preferably a hydrogen atom or a fluorine atom group, because raw materials are easily available and the polymerization reactivity is high.

More specific examples of the fluorine-containing diene compound of the present invention are shown below.

[Chem. 7]

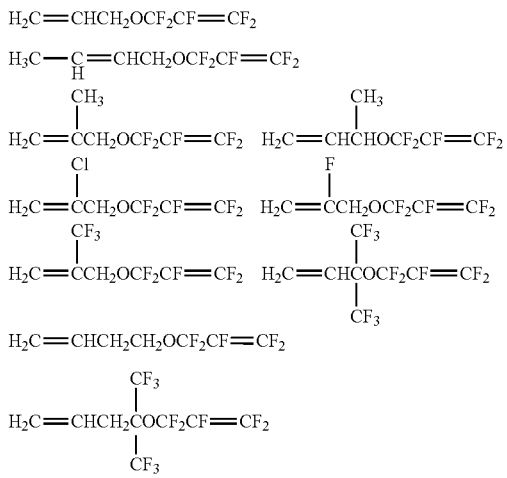

<Production Method of Fluorine-Containing Diene Compound>

The fluorine-containing diene compound represented by the formula I of the present invention can be synthesized by reacting a compound (compound a) represented by the following formula a with a compound (compound b, perfluoroallyl fluorosulfate) represented by the following formula b in the presence of a base and preferably in the presence of a solvent.

[Chem. 8]

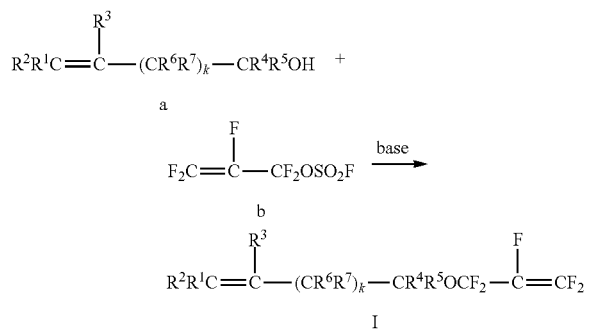

Symbols $R^1$ to $R^7$ and k in the formula a are the same as $R^1$ to $R^7$ and k in the formula I. Preferred embodiments are also the same.

Compound b can be synthesized in one step by reacting hexafluoropropene ($CF_2=CFCF_3$) with fuming sulfuric acid ($SO_3$) in the presence of, for example, trimethyl borate ($B(OCH_3)_3$) or boron trifluoride ($BF_3$).

Compound a acts the same as an alkoxide on the obtained compound b in the presence of a base to cause a reaction as a nucleophilic reagent ($Nu^-$) and elimination of a fluorosulfonate ion as illustrated in the scheme below, and thus, a reaction of compound a with compound b proceeds.

[Chem. 9]

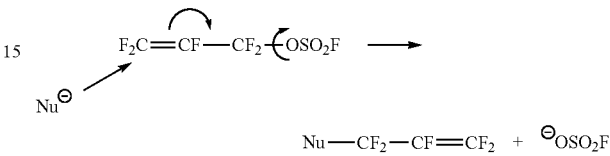

The ratio at which compound a and compound b are charged is not particularly limited and varies depending on the base or solvent used and reaction conditions. For example, the ratio of compound a is preferably 0.7 mol or more relative to 1 mol of compound b, and is more preferably 1 mol or more, because the conversion of compound b increases. From the standpoint of effective utilization of compound a and volumetric efficiency of the reaction, the ratio is preferably 10 mol or less, more preferably 8 mol or less. In the case where, for example, compound a is expensive, the yield of the product based on compound a can be increased by raising the ratio of compound b.

As the base, both an inorganic base such as sodium hydroxide, potassium hydroxide, sodium carbonate and potassium carbonate, and an organic base such as amine type, pyridine type and aniline type can be used. Among others, an organic base is preferred for the reason that it is soluble in a solvent, the reaction uniformly proceeds, and the reaction selectivity is high. The base is more preferably a tertiary amine, still more preferably an aliphatic tertiary amine.

The aliphatic tertiary amine includes triethylamine, tripropylamine, etc. The tertiary amine may contain a ring structure or may contain a plurality of tertiary amine structures in the molecule.

Non-Patent Literature 1 states that perfluoroallyl fluorosulfate reacts with various alcohols or metal alkoxides. However, it does not mention that the reaction of an alcohol with perfluoroallyl fluorosulfate proceeds in the presence of an organic base, particularly, an aliphatic tertiary amine. On the other hand, it has been newly found that in the production method of the present invention, the selectivity more increases when using an organic base, particularly, an aliphatic tertiary amine, than when using an inorganic base.

Addition of a base is preferred, because the reaction speed increases and the selectivity of the target compound also increases. The amount of the base varies depending on the type of the base used or other conditions but is, for example, preferably 0.5 mol or more, more preferably 1 mol or more, relative to 1 mol of compound b. In the case of using an organic base, if the amount of the organic base is too large, the volumetric efficiency of the reaction decreases, and this is disadvantageous in view of cost. For this reason, the amount is preferably 2 mol or less. In the case of an inorganic base, the base can be added in a larger amount, compared with an organic base, but, on the other hand, use of an organic base, particularly, an aliphatic tertiary amine, is preferred from the viewpoint of selectivity as described above.

The solvent is not particularly limited as long as it is an aprotic and polar solvent, but a solvent containing at least either one of glyme and nitrile can be preferably used because it is a liquid at room temperature and is easy to handle. As the glyme, monoglyme, diglyme, triglyme, and tetraglyme are more preferred, and as the nitrile, acetonitrile, adiponitrile, and benzonitrile are more preferred. One of these solvents may be used, or a mixture of a plurality of kinds thereof may be used.

The reaction of compound a, compound b and a base in the presence of a solvent is performed while stirring the solution and sufficiently proceeds at a temperature near room temperature. Among others, the reaction temperature is preferably 0° C. or higher in view of the reaction speed and is preferably 40° C. or lower from the viewpoint of preventing a rapid violent reaction. The reaction temperature is more preferably 20° C. or lower, still more preferably 10° C. or lower. After the reaction has almost proceeded, the temperature is allowed to rise a little higher than that.

The reaction time is not particularly limited but is, for example, approximately from 1 hour to 1 day. The reaction may also be stopped while performing identification of the obtained compound by means of gas chromatography, etc. and seeing the results.

The reaction pressure is not particularly limited, and the reaction may be performed under atmospheric pressure or applied pressure or the reaction may be performed under reduced pressure. From the viewpoint of preventing rapid heat generation due to heat of reaction and preventing a side reaction, compound b is preferably added continuously or added intermittently to a reaction vessel to which compound a and a base have been added. Therefore, the reaction operation is easier under atmospheric pressure. In the case of performing the reaction under reduced pressure, the pressure is preferably not less than the vapor pressure of the reaction solution, and in the case of applying a pressure, the pressure is preferably 1 MPa or less.

The reaction atmosphere is preferably an inert gas atmosphere. The inert gas includes nitrogen and argon.

From the viewpoint of enhancing the yield of the target product, compound a and compound b are preferably used after dehydration. The dehydration operation is not particularly limited, but usually, the compound is put into contact with a molecular sieve, etc.

The fluorine-containing diene compound obtained by the reaction using an organic base can be made to have a high purity, for example, by removing the polar solvent by washing with water and subjecting the residue to drying with a molecular sieve, etc. and distillation. Or the target product is distilled into a cooled receiver under reduced pressure, being heated if necessary, and contacted with an acid such as hydrochloric acid to remove the organic base contained in the distillate, and a high purity can thereby be efficiently achieved with increased isolated yield. In the case of intending to further increase the purity, precision distillation should be performed.

The obtained fluorine-containing diene compound is unstable depending on its structure and sometimes decomposes and deteriorates even at room temperature. Furthermore, the compound sometimes decomposes and deteriorates at the time of distillation. Accordingly, a stabilizer is added, if desired, to the fluorine-containing diene compound.

The stabilizer is preferably a basic substance, and both an inorganic base and an organic base can be used. Examples of the inorganic base include $NaHCO_3$, $KHCO_3$, $Na_2CO_3$, $K_2CO_3$, $Mg_{0.7}Al_{0.3}O_{1.15}$, etc. Examples of the organic base include an aliphatic amine, an aromatic amine, and a heterocyclic amine.

In the case where the stabilizer is added during storage before purification of the fluorine-containing diene compound and the stabilizer is separated by distillation or hydrochloric acid treatment after the storage, an organic amine giving good storage stability is preferred. In the case of distillation purification, it is preferable to select an organic amine having a boiling point that is far from the boiling point of the fluorine-containing diene compound. As the organic amine, a diamine such as N,N,N',N'-tetraethylethylenediamine and 4,4'-bipyridyl may also be selected. In the case where the addition of an aliphatic amine causes a deterioration of the fluorine-containing diene compound, an aromatic amine is preferably used.

After the distillation, an inorganic base is preferably used as the stabilizer. The inorganic base does not dissolve in the fluorine-containing diene compound, and this facilitates separation when the fluorine-containing diene compound is actually used. The fluorine-containing diene compound before distillation and after distillation is preferably stored by cooling it in a refrigerator or a freezer. The fluorine-containing diene compound is more stable at a lower temperature. Storage at 10° C. or lower is preferred, and storage at −20° C. or lower is more preferred.

Furthermore, the fluorine-containing diene compound is preferably stored in an inert gas atmosphere such as nitrogen gas and argon gas. The inorganic base added as the stabilizer can be separated and removed by filtration or vacuum distillation before polymerization.

The obtained fluorine-containing diene compound can be identified by a conventionally known method and, for example, can be identified by $^1H$-, $^{13}C$-, and $^{19}F$-NMR measurements.

<Fluorine-Containing Polymer>

A fluorine-containing polymer is obtained by polymerizing a fluorine-containing compound represented by the formula I' as a raw material monomer. The fluorine-containing compound represented by the formula I' has a cyclopolymerization reactivity, and a fluorine-containing polymer having a ring structure in the main chain is obtained.

[Chem. 10]

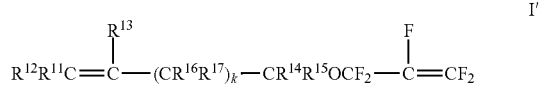

In the formula, each of $R^{11}$ to $R^{17}$ is independently a hydrogen atom, a chlorine atom, a fluorine atom, or a monovalent organic group which may have a heteroatom, k is 0 or 1, at least one of $R^{11}$ to $R^{17}$ is a hydrogen atom, $R^{11}$ or $R^{12}$ may combine with any one of $R^{13}$ to $R^{17}$ to form a ring, and $R^{13}$ may combine with any one of $R^{11}$, $R^{12}$ and $R^{14}$ to $R^{17}$ to form a ring. The heteroatom includes an oxygen atom, a nitrogen atom, and a sulfur atom, and introduction of an oxygen atom is easiest. The monovalent organic group is preferably a monovalent organic group having a carbon number of 1 to 5, more preferably a monovalent hydrocarbon group or monovalent fluoroalkyl group having a carbon number of 1 to 3, still more preferably a methyl group or a trifluoromethyl group.

In the formula I', since at least one of $R^{11}$ to $R^{17}$ is a hydrogen atom, the fluorine-containing compound above is a partially fluorinated compound and is not a perfluoro compound.

The fluorine-containing compound represented by the formula I' is preferably a fluorine-containing diene compound represented by the formula I.

As with the fluorine-containing diene compound represented by the formula I, the fluorine-containing compound represented by the formula I' can be synthesized by reacting a compound (compound a') represented by the following formula a' with a compound (compound b, perfluoroallyl fluorosulfate) represented by the following formula b in the presence of a base and preferably further in the presence of a solvent.

[Chem. 11]

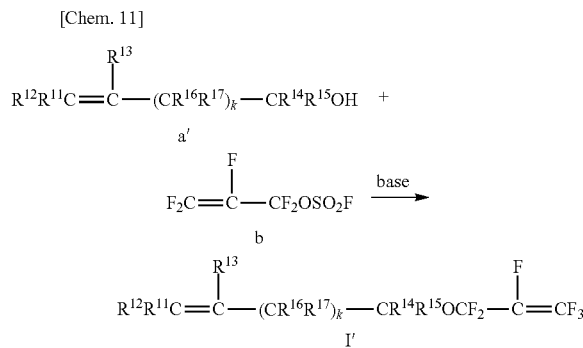

Out of $R^{11}$ to $R^{15}$, each of $R^{11}$ and $R^{12}$ is independently, preferably a hydrogen atom, a fluorine atom, a methyl group, or a trifluoromethyl group, because the polymerization reactivity of the fluorine-containing compound increases, and is more preferably a hydrogen atom or a fluorine atom.

$R^{13}$ is preferably a hydrogen atom, a chlorine atom, a fluorine atom, a methyl group, or a trifluoromethyl group, because the polymerization reactivity of the fluorine-containing compound increases.

Each of $R^{14}$ and $R^{15}$ is independently, preferably a hydrogen atom, a methyl group, or a trifluoromethyl group, because the compound serving as a raw material at the time of production of the fluorine-containing compound represented by the formula I' is made stable. In the case where $R^{14}$ or $R^{15}$ is a fluorine atom, elimination of hydrogen fluoride (HF) readily occurs and consequently, the structure is likely to be unstable.

Each of $R^{16}$ and $R^{17}$ is independently, preferably a hydrogen atom or a fluorine atom, because the polymerization reactivity is high and raw materials are easily available or synthesized.

Furthermore, in the case of using the obtained fluorine-containing polymer as a photocurable or thermosetting material, the volatility of the fluorine-containing compound represented by the formula I' needs to be suppressed. The method for suppressing the volatility includes, for example, a method of increasing the molecular weight.

Therefore, the molecular weight of the fluorine-containing compound represented by the formula I' is preferably 188 or more and in the case of being used as a photocurable material or a thermosetting material, is more preferably 400 or more. Also, in view of curing reactivity, the upper limit is preferably 5,000 or less, more preferably 2,000 or less, still more preferably 1,000 or less. It is easy and preferable to perform the monomer purification by distillation. From the viewpoint of ensuring a vapor pressure for distillation purification, the molecular weight of the fluorine-containing compound represented by the formula I' is preferably 1,000 or less, more preferably 700 or less, still more preferably 500 or less.

In the cyclopolymerization when k=0 in the formula I', as shown in the scheme below, there may be a case of forming a 5-membered ring and a case of forming a 6-membered ring, and a fluorine-containing polymer containing, as a repeating unit, a structure derived from at least one of these compounds is obtained. In the scheme below, P. denotes a radical such as polymer propagating radical, chain transfer agent-derived radical and initiation radical generated from an initiator.

The polymer may be a homopolymer obtained by polymerizing one kind of monomer or may be a copolymer (interpolymer) obtained by polymerizing a plurality of kinds of monomers. A plurality of kinds of repeating units (for example, a 5-membered ring structure and a 6-membered ring structure) may also be produced from one kind of a monomer.

In the case of a copolymer, the copolymer may be any of a random copolymer, an alternating copolymer, a block copolymer, and a graft copolymer.

The monomer copolymerized with a monomer represented by the formula I' where k=0 may be another monomer having a structure represented by the formula I' or may be another monomer not having a structure represented by the formula I'.

[Chem. 12]

[Chem. 13]

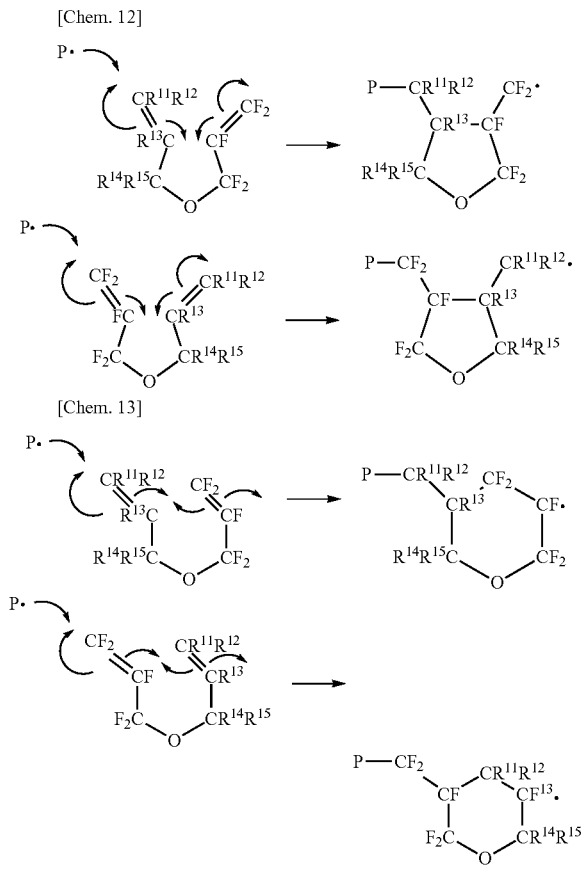

In the cyclopolymerization when k=1 in the formula I', as shown in the scheme below, there may be a case of forming a 6-membered ring and a case of forming a 7-membered ring, and a fluorine-containing polymer containing, as a repeating unit, a structure derived from at least one of these compounds is obtained. Since the ring structure of a 6-membered ring is more stable than that of a 7-membered ring, a 6-membered ring is considered to be preferentially produced. The polymer may be a homopolymer obtained by polymerizing one kind of monomer or may be a copolymer (interpolymer) obtained by polymerizing a plurality of kinds of monomers. A plurality of kinds of repeating units (for example, a 6-membered ring structure and a 7-membered ring structure) may also be produced from one kind of a monomer.

In the case of a copolymer, the copolymer may be any of a random copolymer, an alternating copolymer, a block copolymer, and a graft copolymer.

The monomer copolymerized with a monomer represented by the formula I' where k=1 may be another monomer having a structure represented by the formula I' or may be another monomer not having a structure represented by the formula I'.

[Chem. 14]

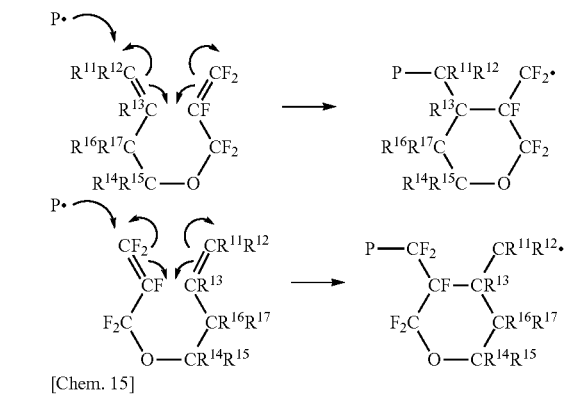

[Chem. 15]

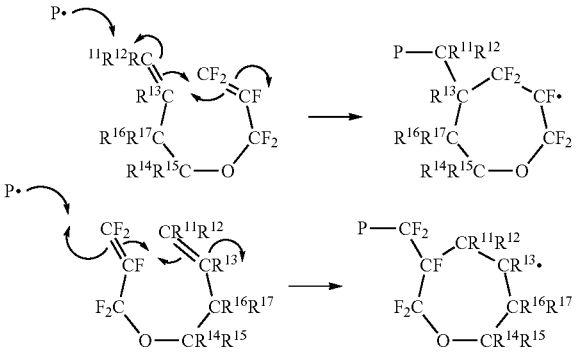

The fluorine-containing compound represented by the formula I' used in the polymerization is preferably a fluorine-containing diene compound represented by the formula I. This compound is preferable in that the polymerization reactivity of the monomer is high and raw materials for the monomer synthesis are easily available.

More specific examples of the repeating unit that the fluorine-containing polymer of the present invention contains are shown below.

[Chem. 16]

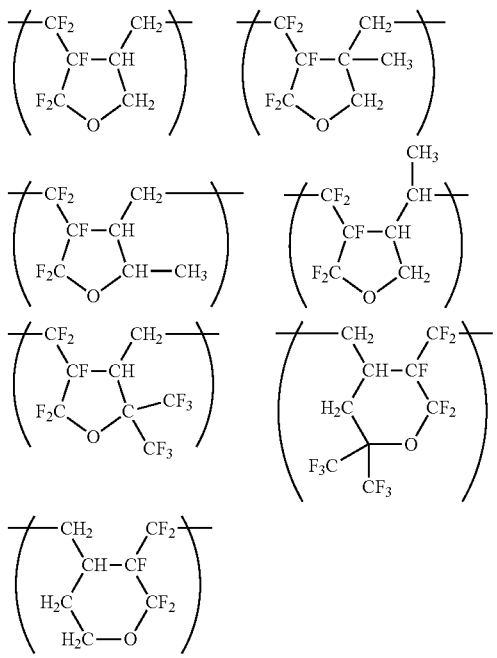

The glass transition temperature (Tg) of the fluorine-containing polymer is, in the case where its shaped article is exposed to a high-temperature environment, preferably higher in view of the shape stability of the material. Tg is, for example, preferably 80° C. or higher, more preferably 125° C. or higher, still more preferably 150° C. or higher. The upper limit is not particularly limited, but in the case of performing hot-melt forming or achieving densification, homogenization, stabilization and strengthening of the structure by heating (annealing) a coating film obtained from a solution of the fluorine-containing polymer at a higher temperature than Tg, the Tg is preferably 250° C. or lower, more preferably 200° C. or lower.

If Tg is too high, the temperature at the time of hot-melt forming or annealing considerably rises, causing concern about the effect on the forming device or peripheral materials of the target article, and such a temperature is undesired also in view of the energy input. Tg can be measured by a differential scanning calorimeter (DSC). The monomer giving a high Tg is preferably a monomer having the following structure.

[Chem. 17]

In the formula, $R^{13'}$ is an alkyl group having a carbon number of 1 to 5 which may be substituted by a fluorine atom. In particular, a monomer where $R^{13'}$ is a methyl group is preferred, because β-methallyl alcohol as a raw material is easily available.

As the monomer giving a high Tg, a monomer having the following structure is also preferred.

[Chem. 18]

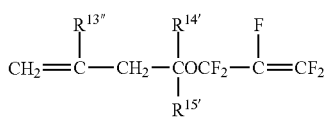

In the formula, $R^{13''}$ is a hydrogen atom or an alkyl group having a carbon number of 1 to 5 which may be substituted by a fluorine atom. Each of $R^{14'}$ and $R^{15'}$ is an alkyl group having a carbon number of 1 to 5 which may be substituted by a fluorine atom, and in particular, a monomer where both $R^{14'}$ and $R^{15'}$ are a trifluoromethyl group is preferred because of good availability of raw materials of the monomer. Among others, a monomer where $R^{13''}$ is a hydrogen atom is more preferred, because the raw materials are easily available.

The thermal decomposition temperature (Td) of the fluorine-containing polymer is preferably higher in view of hot-melt forming and annealing temperature. As in the solder reflow in the production process of an electronic device containing a fluorine-containing polymer, an article containing the fluorine-containing polymer is sometimes exposed to a high temperature in the production process, and therefore, the thermal decomposition temperature is preferably higher. In the present description, Td is a temperature at which a weight loss of 3% is recognized in the thermogravimetric analysis (TGA) measurement.

Td is preferably 270° C. or higher, more preferably 300° C. or higher, still more preferably 350° C. or higher. The upper limit is not particularly limited, but Td of a fluorine-containing polymer is 500° C. or lower in general.

In the case where Td in an inert gas such as nitrogen is higher than Td in air, the polymer can be exposed to a higher temperature in a vacuum or in an inert gas atmosphere than in air.

The fluorine-containing polymer is preferably soluble in a solvent in view of thin-film forming. A liquid composition obtained by dissolving the polymer is cast, and a thin film having a uniform thickness can thereby be obtained. In the present description, the term "soluble in a solvent" means that 0.1 mass % or more of the polymer can be dissolved in the solvent.

As the solvent, the polymer is preferably soluble, for example in tetrahydrofuran, acetone, ethyl acetate, dichloromethane, perfluorobenzene, etc.

In view of mechanical properties and physical properties, the weight average molecular weight in terms of polymethyl methacrylate (PMMA) of the fluorine-containing polymer is preferably 10,000 or more, more preferably 40,000 or more, still more preferably 100,000 or more. On the other hand, in view of formability, the weight average molecular weight is preferably 2,000,000 or less, more preferably 1,000,000 or less, still more preferably 500,000 or less.

The weight average molecular weight of the fluorine-containing polymer can be measured using gel permeation chromatography (GPC) under the polymer solution condition and can be controlled by the amount of initiator, the type and amount of chain transfer agent, the polymerization temperature, etc.

<Production Method of Fluorine-Containing Polymer>

The method for producing a fluorine-containing polymer of the present invention includes a step of polymerizing a raw material monomer containing a fluorine-containing compound represented by the following formula I'. Specifically, the polymer can be synthesized, for example, by dissolving the raw material monomer in a solvent and causing the reaction to proceed by the addition of an initiator.

A copolymer may also be synthesized using a raw material monomer composition further containing a compound other than the fluorine-containing compound represented by the formula I'. In this case, another compound serving as a raw material monomer may be sufficient if it is a compound having an olefin structure, and examples thereof include tetrafluoroethylene, chlorotrifluoroethylene, trifluoroethylene, vinylidene fluoride, vinyl fluoride, ethylene, propylene, perfluoroa-olefins (e.g., hexafluoropropylene), (perfluoroalkyl)ethylenes (e.g., (perfluorobutyl)ethylene, (perfluorohexyl)ethylene), (perfluoroalkyl)propenes (e.g., 3-perfluorohexyl-1-propene, 3-perfluorooctyl-1-propene), perfluoro(2,2-dimethyl-1,3-dioxole), perfluoro(1,3-dioxole), perfluoro(2-methylene-4-methyl-1,3-dioxolane), perfluoro(4-methoxy-1,3-dioxole), and a perfluorovinyl ether such as perfluoro(alkyl vinyl ether) and perfluoro(ethereal oxygen atom-containing alkyl vinyl ether).

As the perfluorovinyl ethers, a compound represented by $CF_2=CF-(OCF_2CFZ)_t-O-R^f$ is preferred. In the formula, t is an integer of 0 to 3, Z is a fluorine atom or a trifluoromethyl group, and $R^f$ is a perfluoroalkyl group having a carbon number of 1 to 12 which may have a linear structure or a branched structure. Among others, compounds (i) to (iii) represented by the following formulae (i) to (iii) are preferred. In the formulae, v is an integer of 1 to 9, w is an integer of 1 to 9, and x is 2 or 3.

[Chem. 19]

 (i)

 (ii)

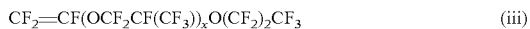 (iii)

In addition to those described above, examples further include fluorine-free alkyl vinyl ethers such as ethyl vinyl ether, propyl vinyl ether and cyclohexyl vinyl ether, acrylates such as methyl acrylate, ethyl acrylate, 1H-1H-2H-2H-perfluorohexyl acrylate, 1H-1H-2H-2H-perfluorooctyl acrylate, methyl 2-fluoroacrylate and methyl 2-chloroacrylate, methacrylates such as methyl methacrylate, ethyl methacrylate, 1H-1H-2H-2H-perfluorohexyl methacrylate, 1H-1H-2H-2H-perfluorooctyl methacrylate and methyl 2-(trifluoromethyl)acrylate, acrylonitrile, vinyl acetate, styrene, cyclic olefin, etc.

A monomer having a hydroxyl group or a functional group such as an epoxy group serving as a crosslinking site can also be copolymerized. The monomer having a hydroxyl group includes hydroxyethyl methacrylate, hydroxyethyl acrylate, hydroxyethyl vinyl ether, etc. The monomer having an epoxy group includes glycidyl methacrylate, glycidyl acrylate, glycidyl allyl ether, 3,4-epoxycyclohexylmethyl methacrylate, (3-ethyloxetan-3-yl)methyl methacrylate, etc. An acid anhydride having a radical polymerization reactive double bond, such as maleic anhydride, itaconic anhydride and 5-norbornene-2,3-dicarboxylic anhydride, may also be copolymerized.

As the copolymer obtained, for example, a random copolymer, an alternating copolymer, a block copolymer, and a graft copolymer can be synthesized, and a desired copolymer can be obtained by controlling the ratio at which raw material monomers are charged, or the polymerization conditions.

As for the raw material monomer, the fluorine-containing compound represented by the formula I' may be used as a main monomer or may be used as a comonomer but is preferably used as a main monomer in view of low refractive index, low dielectric constant, chemical durability and liquid repellency. The copolymer may be obtained as a multicomponent copolymer, i.e., a ternary or higher copolymer, by using two or more kinds of other olefin compounds.

From the viewpoint of utilizing the polymer physical properties provided by the repeating unit derived from the fluorine-containing compound represented by the formula I', the proportion of the repeating unit derived from the fluorine-containing compound in the copolymer is preferably 50 mol % or more, more preferably 70 mol % or more, particularly preferably 85 mol % or more. The fluorine-containing compound represented by the formula I' may be one kind, or a plurality of kinds of compounds may be used. In the latter case, the total proportion of the repeating units derived from the fluorine-containing compounds represented by the formula I' is preferably within the above range.

The polymerization reaction is not particularly limited as long as it is performed under the conditions generating a radical. The method therefor includes, for example, known radical polymerization methods such as bulk polymerization method, solution polymerization method, suspension polymerization method and emulsion polymerization method. The polymerization may be performed in liquid or supercritical carbon dioxide.

The polymerization is performed under the conditions generating a radical. The method for generating a radical includes a method of performing irradiation with radiation such as ultraviolet ray, γ ray, electron beam, etc., and a method of adding a radical initiator. In the case of adding a radical initiator in a polymerization reactor, the polymerization temperature is usually from 10 to 150° C., preferably from 15 to 100° C. The polymerization time is usually from 1 to 24 hours, preferably from 2 to 10 hours. The polymerization can also be performed using a photoradical initiator by performing irradiation with visible light or ultraviolet ray. In the case of performing irradiation with radiation at the time of curing of the coating film, the irradiation time is approximately from 0.1 seconds to 10 minutes, and, usually, a photoradical initiator such as 1-hydroxycyclohexyl phenyl ketone is added.

The radical initiator includes bis(fluoroacyl) peroxides, bis(chlorofluoroacyl) peroxides, dialkyl peroxydicarbonates, diacyl peroxides, peroxyesters, azo compounds, persulfates, etc. It is preferable to use a nonionic radical initiator soluble in a solvent or monomer in the case of a bulk polymerization method, a solution polymerization method and a suspension polymerization method. It is preferable to use a water-soluble radical initiator such as persulfates in the case of an emulsion polymerization method.

The amount of the initiator is appropriately determined by taking into account the type of initiator, the type of monomer, the type and amount of chain transfer agent (molecular weight adjusting agent), the polymerization speed, the molecular weight of target polymer, the polymerization temperature, etc. For, example, the amount of the initiator is determined such that in the synthesis of a polymer having the target molecular weight, the polymerization time falls within the range of preferably from 1 to 24 hours, more preferably from 2 to 10 hours.

The solvent used in the solution polymerization method is preferably a solvent having a boiling point of 20 to 350° C., more preferably a solvent having a boiling point of 40 to 150° C. Among others, a solvent having a boiling point of 50 to 80° C. is preferred from the viewpoint of separating the solvent from the polymer and recovering the solvent.

In the solution polymerization method, a monomer, a nonionic radical initiator, etc. are added to a solvent, and polymerization of the monomer is performed by generating a radical in the solvent. The addition of the monomer and initiator may be batch addition, may be sequential addition, or may be continuous addition.

In the suspension polymerization method, water is used as a dispersion medium, and a monomer, a nonionic radical initiator, etc. are added to the dispersion medium to perform the polymerization of the monomer.

Examples of the nonionic radical initiator include bis (fluoroacyl) peroxides, bis(chlorofluoroacyl) peroxides, dialkyl peroxydicarbonates, diacyl peroxides, peroxyesters, dialkyl peroxides, bis(fluoroalkyl) peroxides, azo compounds, etc. In the suspension polymerization method, the solvent above and a surfactant, etc. may be added respectively as an auxiliary agent and as a dispersion stabilizer for preventing aggregation of suspended particles.

The solvent is preferably a solvent causing little chain transfer to the solvent and is not particularly limited as long as it does not adversely affect the reaction, and a fluorine-free organic solvent, a fluorine-containing solvent, an ionic liquid, water, etc. can be used individually or as a mixture. A part or all of hydrogen atoms in the solvent molecule may be replaced by a deuterium atom.

Furthermore, in the case where the raw material monomer is a liquid (encompassing the case of being liquefied by heating), bulk polymerization can be employed without using a solvent.

The solvent is preferably a fluorine-containing organic solvent and examples thereof include perfluorotrialkylamines (e.g., perfluorotributyl amine), perfluorocarbons (e.g., perfluorohexane, perfluorooctane), hydrofluorocarbons (e.g., 1H,4H-perfluorobutane, 1H-perfluorohexane, 1,1,1,3,3-pentafluorobutane, 1,1,2,2,3,3,4-heptafluorocyclopentane, 2H,3H-perfluoropentane), hydrochlorofluorocarbons (e.g., 3,3-dichloro-1,1,1,2,2-pentafluoropropane, 1,3-dichloro-1,1,2,2,3-pentafluoropropane (HCFC-225cb)), hydrofluoroethers (e.g., $CF_3CH_2OCF_2CF_2H$, (perfluorobutoxy)methane, (perfluorobutoxy)ethane), fluorine-containing aromatic compounds (e.g., perfluorobenzene, m-bis(trifluoromethyl)benzene, p-bis(trifluoromethyl)benzene), etc. A fluorine-free organic solvent can also be used, but its use tends to decrease the molecular weight of the polymer due to the chain transfer effect.

As the ionic liquid, for example, various pyridinium salts, various imidazolium salts, etc can be used.

In view of reproducibility of the polymerization reaction and enhancement of the yield of the target product, the solvent is preferably used after deoxygenating (deaerating) it. The deaerating operation is not particularly limited, and freeze-pump-thaw degassing, etc. is sometimes performed. An operation of expelling oxygen by bubbling an inert gas such as nitrogen gas is performed in some cases. On this occasion, when the boiling point of the solvent is low, an effort needs to be made to avoid volatilization of the solvent due to entrainment with the inert gas by previously cooling the solvent etc. or recover the entrained and volatilized solvent.

In the polymerization reaction, a chain transfer agent or a terminator may also be used so as to control the molecular weight or molecular weight distribution.

As the molecular weight adjuster, the chain transfer agent is preferably a hydrocarbon-based compound, and examples thereof include hexane, methanol, isopropyl alcohol, monoglyme, etc.

In the case of performing the polymerization by heating in the polymerization using a radical initiator, the polymerization can be terminated by cooling, but it is also possible to add a terminator at the end of polymerization.

As the terminator, for example, quinones such as para-benzoquinone and 2,5-di-tert-butylbenzoquinone, hydroquinone, phenols such as 4-methoxyphenol and 2-(1,1-dimethylethyl)-4,6-dimethylphenol, sulfur-containing compounds such as phenothiazine, thiourea and sodium N,N-diethyldithiocarbamate, nitroso compounds such as N-nitrosodiphenyl amine and N-nitrosophenylhydroxylamine aluminum salt, piperidine-1-oxyls such as 4-hydroxy-2,2,6,6-tetramethylpiperidine-1-oxyl, transition metal compounds such as copper acetate, copper dialkyldithiocarbamate and manganese acetate can be used.

In view of the yield of the target polymer and the enhanced reproducibility of the polymerization reaction or the stability of the monomer, the monomer as a raw material is preferably used after deoxygenating (deaerating) it. The monomer is dehydrated by the addition of a desiccant (e.g., molecular sieve, magnesium sulfate, sodium sulfate, calcium chloride) or by the distillation purification, but in addition to the dehydration, a deoxygenation (deaerating) operation may further be performed. In the further deoxygenation (deaerating) operation, the same method as that for the operation of deoxygenating (deaerating) the above-described solvent may be used.

Furthermore, by freeze-pump-thaw degassing operation, etc. after charging the raw material monomer into a reaction vessel together with an initiator and a solvent, it can be degassed (deoxygenated) together with the initiator, solvent, etc. Deoxygenation may also be performed by repeating pressurization with an inert gas such as nitrogen gas and purging. If desired, depressurization may be performed after purging. Deoxygenation may also be performed by repeating the depressurization operation and the introduction of an inert gas (e.g., nitrogen gas) at atmospheric pressure.

A raw material monomer, an initiator and a solvent are charged into a reaction vessel and, if desired, deaeration is performed, and the polymerization reaction is allowed to proceed. The polymerization is preferably performed in an inert gas atmosphere such as nitrogen gas.

In the case of synthesizing a copolymer, two or more kinds of monomers as raw materials may be previously mixed and then charged into a reaction vessel or may be charged separately.

The polymerization reaction can be terminated by cooling or by charging a terminator.

After the completion of the polymerization reaction, the residual monomer can be removed by a known method, and the target fluorine-containing polymer can be isolated by a known method.

The isolation method includes, for example, in the case of solution polymerization, a method where the reaction solution is discharged into a poor solvent while stirring and the polymer is coagulated to form a slurry and recovered by a filtration method, a centrifugation method, a decantation method, etc., a steam stripping method where steam is brown into the reaction solution to precipitate the polymer, and a method where the solvent is directly removed from the reaction solution by heating, etc., and in some cases, a method of adding a poor solvent to the reaction solution is employed. In the case of a slurry formed by coagulation of the polymer, the method includes a method where the polymer is directly recovered by a filtration method, a centrifugation method, a decantation method, etc. Other methods include column chromatography, recycling preparative HPLC, etc., and these may be used individually or in combination of a plurality thereof, if desired.

The target product obtained by this reaction can be identified by the same known method as that for ordinary polymer compounds. The method includes, for example, $^1$H-, $^{19}$F- and $^{13}$C-NMRs, two-dimensional NMR, GPC, static light scattering, SIMS, GC-MS, etc., and these may be used individually or in combination of a plurality thereof, if desired.

The obtained fluorine-containing polymer has properties such as high heat resistance, low water absorptivity, high light transmittance (transparency), low dielectric constant, low refractive index, high chemical durability, high weather resistance, high liquid repellency and low adhesion and also has an excellent balance of these various properties. Accordingly, the polymer can be utilized in a wide variety of fields including, for example, an electric/electronic material used as an insulating material for an interlayer insulating film, etc. in an electronic circuit board or semiconductor, an optical material such as optical waveguide, core material and clad material of optical fiber, light guide plate and lens, a low-refractive-index charge transport layer material for increasing light extraction efficiency of an organic light-emitting diode, an encapsulating material for various electronic•optical devices, a medical device•cell culture material, a liquid-repellent material, and an elastomer material.

EXAMPLES

The present invention is described specifically below by referring to Examples, but the present invention is not limited thereto.

<Evaluation Method>

In this Example, various properties of the synthesized fluorine-containing diene compound and fluorine-containing polymer were measured by the following methods.

<Structural Analysis>

The structures of the obtained compound and polymer were identified by performing $^1$H-NMR, $^{13}$C-NMR and $^{19}$F-NMR measurements with a nuclear magnetic resonance apparatus (JNM-AL300 or ECA600) manufactured by JEOL Ltd. or conducting an analysis using two-dimensional NMR of these measurements. The reference materials of $^1$H-NMR and $^{19}$F-NMR chemical shifts are tetramethylsilane and $CFCl_3$, respectively.

(Weight Average Molecular Weight)

As for the weight average molecular weight of the polymer, the weight average molecular weight in terms of PMMA was determined using a gel permeation chromatography (GPC) measuring apparatus (manufactured by Tosoh Corporation, HLC-8320GPC). As the solvent, ASAHIKLIN AK-225 SEC Grade -1 produced by AGC Inc. was used. As the column, two PLgel 5 µm MIXED-C columns (produced by Polymer Laboratories Ltd.) were used by connecting them in series. The measurement temperature was set to 40° C. As the detector, an evaporative light scattering detector was used.

(Thermal Decomposition Temperature Td)

Using Thermogravimetry/Differential Thermal Analyzer STA7200 (Hitachi High-Tech Science Corporation) by raising the temperature at 10° C./min in dry air or in nitrogen, a 3% weight loss temperature Td (3%) was determined.

(Glass Transition Temperature Tg)

In the measurement of Tg, a DSC apparatus (unit name: Q100, manufactured by TA Instruments, or unit name: DSC 204 F1 Phoenix, manufactured by NETZSCH) was used. The polymer was put in an aluminum-made container for a differential scanning calorimeter (DSC) and after raising the temperature to a temperature higher by at least 30° C. than the measured Tg, cooled to −50° C. at 10° C./min. Subsequently, the polymer was heated to a temperature higher by at least 30° C. than the transition end temperature by raising the temperature at 10° C./min, and a DSC curve was drawn to determine Tg (midpoint glass transition temperature).

The glass transition temperature of the polymers produced in Examples 2-1 to 2-14 and 2-16 was measured using the apparatus manufactured by TA Instruments, and the glass transition temperature of the polymers produced in Examples 2-15 and 2-17 to 2-21 was measured using the apparatus manufactured by NETZSCH.

Abbreviations of the compounds used in Examples are as follows.
(Reagent)
PFAS: perfluoroallyl fluorosulfate ($CF_2$=$CFCF_2OSO_2F$)
(Monomer)
FHDAE: $CH_2$=$CHCH_2OCF_2CF$=$CF_2$
1M-FHDAE: $CH_3$—$CH$=$CHCH_2OCF_2CF$=$CF_2$
2M-FHDAE: $CH_2$=$C(CH_3)CH_2OCF_2CF$=$CF_2$
3M-FHDAE: $CH_2$=$CHCH(CH_3)OCF_2CF$=$CF_2$
33DFM-FHDAE: $CH_2$=$CHC(CF_3)_2OCF_2CF$=$CF_2$
FHBAE: $CH_2$=$CHCH_2CH_2OCF_2CF$=$CF_2$
44DFM-FHBAE: $CH_2$=$CHCH_2C(CF_3)_2OCF_2CF$=$CF_2$
C6FMA: $CH_2$=$C(CH_3)COO(CH_2)_2(CF_2)_6F$
(Radical Initiator)
IPP: diisopropyl peroxydicarbonate
PFBPO: perfluorobenzoyl peroxide (compound represented by the following formula)

[Chem. 20]

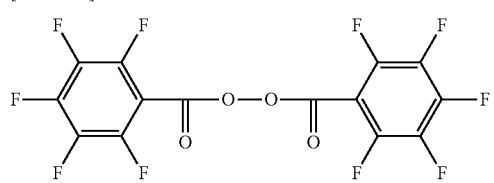

(Solvent)
HCFC-225cb: $CClF_2CF_2CHClF$

Example 1-1

Synthesis 1 of FHDAE

Diglyme (13.5 g) dehydrated with molecular sieve 4A, sodium carbonate (1.09 g, 10.3 mmol) and allyl alcohol (9.00 g, 155 mmol) were charged in a nitrogen atmosphere into a 50 mL four-neck round bottom flask equipped with a reflux condenser, a dropping funnel and a thermometer and cooled in ice water while stirring with a stir bar until the internal temperature became 5° C. or lower. While keeping the internal temperature at 15° C. or lower, PFAS (4.50 g, 19.6 mmol) was added dropwise over 15 minutes. The internal temperature at the end of dropwise addition was 2° C. After ice was removed from the ice water bath and the solution was stirred for 5 hours, the internal temperature was 12° C. The reaction yield of FHDAE was determined from the gas chromatograph (GC) analysis of the reaction solution and found to be 65%.

The area ratio of FHDAE to diallyl ether ($CH_2$=$CHCH_2OCH_2CH$=$CH_2$) produced as a by-product was 26:1. The reaction yield was calculated utilizing the sensitivity ratio of gas chromatography peaks determined using FHDAE obtained afterward by distillation purification and using diglyme. The conversion of PFAS was 100%. The same reaction was performed, and the reaction solution was washed with water three times, dried by molecular sieve 4A and after adding 4,4'-bipyridyl, distilled to obtain FHDAE having a boiling point of 45.8° C./26.6 kPa and a GC purity of 99% or more.

$^1$H-NMR ($CDCl_3$): δ (ppm) 4.48 (2H), 5.28 (1H), 5.38 (1H), 5.92 (1H).
$^{19}$F-NMR ($CDCl_3$): δ (ppm) −73.7 (2F), −95.3 (1F), −107.4 (1F), −189.4 (1F)

Example 1-2

Synthesis 2 of FHDAE

Tetraglyme (60.8 g) dehydrated with molecular sieve 4A, triethylamine (10.7 g, 106 mmol) and allyl alcohol (6.13 g, 106 mmol) were charged in a nitrogen atmosphere into a 200 mL four-neck round bottom flask equipped with a reflux condenser, a dropping funnel and a thermometer and cooled in ice water while stirring with a stir bar until the internal temperature became 5° C. or lower. While keeping the internal temperature at 10° C. or lower, PFAS (20.3 g, 88.0 mmol) was added dropwise over 30 minutes. The internal temperature at the end of dropwise addition was 7° C. After ice was removed from the ice water bath and the solution was stirred for 5 hours, the internal temperature was 18° C. As a result of GC analysis of the reaction solution, the conversion of PFAS was 100%, and the reaction yield of FHDAE was 71%. Diallyl ether was not produced. The reaction yield was calculated utilizing the sensitivity ratio of gas chromatography peaks determined using FHDAE obtained by distillation purification and using tetraglyme.

Example 1-3

Synthesis 3 of FHDAE

Tetraglyme (60.8 g) dehydrated with molecular sieve 4A, tripropylamine (15.1 g, 106 mmol) and allyl alcohol (6.13 g, 106 mmol) were charged in a nitrogen atmosphere into a 200 mL four-neck round bottom flask equipped with a reflux condenser, a dropping funnel and a thermometer and cooled in ice water while stirring with a stir bar until the internal temperature became 5° C. or lower. While keeping the internal temperature at 10° C. or lower, PFAS (20.3 g, 88.0 mmol) was added dropwise over 25 minutes. The internal temperature at the end of dropwise addition was 8° C. After ice was removed from the ice water bath and the solution was stirred for 1 hour, the internal temperature was 15° C. Subsequently, the reaction was allowed to proceed at room temperature overnight.

The dropping funnel and the reflux condenser were removed, a water bath at room temperature was set to the four-neck flask and the flask was connected to a vacuum pump via a cooling trap cooled with dry ice-ethanol and a cooling trap cooled with liquid nitrogen, and low-boiling-point components were distilled into the cooling trap while stirring. As a result, 13.7 g of FHDAE containing a small amount of tripropylamine was obtained in the cooling trap cooled with dry ice-ethanol. Diallyl ether was not contained. This crude product was treated with 1 N HCl and then washed with water, and FHDAE not containing tripropylamine was thereby obtained with a GC purity of 99.5%. The yield of the target product was 12.2 g, and the isolation yield was 74%.

Example 1-4

Synthesis of 2M-FHDAE

Tetraglyme (182 g) dehydrated with molecular sieve 4A, tripropylamine (45.4 g, 317 mmol) and β-methallyl alcohol (22.8 g, 317 mmol) were charged in a nitrogen atmosphere into a 1 L four-neck round bottom flask equipped with a reflux condenser, a dropping funnel and a thermometer and cooled in ice water while stirring with a stir bar until the internal temperature became 5° C. or lower. While keeping the internal temperature at 10° C. or lower, PFAS (60.8 g, 264 mmol) was added dropwise over 40 minutes. The internal temperature at the end of dropwise addition was 9° C. After ice was removed from the ice water bath and the solution was stirred for 1 hour, the internal temperature was 16° C. Subsequently, the reaction was allowed to proceed at room temperature overnight. As a result of GC analysis of the reaction solution, the conversion of PFAS was 100%, and the reaction yield of 2M-FHDAE was 81%. The reaction yield was calculated utilizing the sensitivity ratio of gas chromatography peaks determined using 2M-FHDAE obtained by distillation purification and using tetraglyme. After the reaction, the reaction solution was washed with water, treated with 1 N HCl, again washed with water, and distilled. As a result, 2M-FHDAE having a boiling point of 52.4° C./16 kPa and a GC purity of 99.5% or more was obtained.

$^1$H-NMR (CDCl$_3$): δ (ppm) 1.79 (3H), 4.39 (2H), 4.98 (1H), 5.05 (1H)
$^{19}$F-NMR (CDCl$_3$): δ (ppm) −73.7 (2F), −95.2 (1F), −107.4 (1F), −189.4 (1F)

Example 1-5

Synthesis of 1M-FHDAE

Tetraglyme (60.8 g) dehydrated with molecular sieve 4A, tripropylamine (15.1 g, 106 mmol) and crotyl alcohol (7.62 g, 106 mmol) were charged in a nitrogen atmosphere into a 200 mL four-neck round bottom flask equipped with a reflux condenser, a dropping funnel and a thermometer and cooled in ice water while stirring with a stir bar until the internal temperature became 5° C. or lower. While keeping the internal temperature at 10° C. or lower, PFAS (20.3 g, 88.0 mmol) was added dropwise over 40 minutes. The internal temperature at the end of dropwise addition was 9.8° C. After ice was removed from the ice water bath and the solution was stirred for 1 hour, the internal temperature was 16° C. Subsequently, the reaction was allowed to proceed at room temperature overnight. After the reaction, the reaction solution was washed with water, treated with 1 N HCl, and again washed with water. As a result, 1M-FHDAE having a GC purity of 89% was obtained in a yield of 67%.

$^1$H-NMR (CDCl$_3$): δ (ppm) 1.75 (3H), 4.41 (2H), 5.58 (1H), 5.87 (1H)
$^{19}$F-NMR (CDCl$_3$): δ (ppm) −73.5 (2F), −95.5 (1F), −107.5 (1F), −189.2 (1F)

Example 1-6

Synthesis of 3M-FHDAE

Tetraglyme (91.1 g) dehydrated with molecular sieve 4A, triethylamine (16.0 g, 158 mmol) and 1-buten-3-ol (8.57 g, 119 mmol) were charged in a nitrogen atmosphere into a 300 mL four-neck round bottom flask equipped with a reflux condenser, a dropping funnel and a thermometer and cooled in ice water while stirring with a stir bar until the internal temperature became 10° C. or lower. While keeping the internal temperature at 10° C. or lower, PFAS (30.4 g, 6,132 mmol) was added dropwise over 45 minutes. The internal temperature at the end of dropwise addition was 7° C. After ice was removed from the ice water bath 30 minutes after the completion of dropwise addition and the solution was stirred for 30 minutes, the internal temperature was 7° C. Subsequently, the reaction was allowed to proceed at room temperature overnight. When 0.9 g (4 mmol) of PFAS was added and the solution was stirred at room temperature for one day, the conversion of PFAS was 100%.

The dropping funnel and the reflux condenser were removed, a water bath at room temperature was set to the four-neck flask and the flask was connected to a vacuum pump via a cooling trap cooled with dry ice-ethanol and a cooling trap cooled with liquid nitrogen, and low-boiling-point components were distilled into the cooling trap while stirring. After the water bath temperature was kept at room temperature (about 20° C.) for 1 hour, the water bath temperature was raised sequentially to 30° C., 40° C. and 50° C. and kept at each temperature for 30 minutes and at 60° C. for 2 hours. As a result, 21.4 g of 3M-FHDAE containing a small amount of triethylamine was obtained in the dry ice-ethanol cooling trap. This crude product was treated with 1 N HCl and then washed with water, and 3M-FHDAE not containing triethylamine was thereby obtained with a GC purity of 96.9%. The yield of the target product was 15.6 g, and the isolation yield was 65%.

$^1$H-NMR (CDCl$_3$): δ (ppm) 1.39 (3H), 4.92 (1H), 5.17 (1H), 5.27 (1H), 5.88 (1H)
$^{19}$F-NMR (CDCl$_3$): δ (ppm) −73.0 (2F), −95.8 (1F), −107.5 (1F), −188.9 (1F)

Example 1-7

Synthesis of 33DFM-FHDAE

Tetraglyme (45.6 g) dehydrated with molecular sieve 4A, tripropylamine (11.4 g, 79.2 mmol) and CH$_2$=CHC(CF$_3$)$_2$OH (produced by SYNQUEST LABORATORIES) (15.4 g, 79.2 mmol) were charged in a nitrogen atmosphere into a 200 mL four-neck round bottom flask equipped with a reflux condenser, a dropping funnel and a thermometer and cooled in ice water while stirring with a stir bar until the internal temperature became 5° C. or lower. While keeping the internal temperature at 10° C. or lower, PFAS (15.2 g, 66.0 mmol) was added dropwise over 20 minutes. The internal temperature at the end of dropwise addition was 8° C. The internal temperature lowered to 4° C. after 15 minutes. After ice was removed from the ice water bath and the solution was stirred for 1 hour, the internal temperature was 6° C. Subsequently, the reaction was allowed to proceed at room temperature overnight.

The dropping funnel and the reflux condenser were removed, a water bath at room temperature was set to the four-neck flask and the flask was connected to a vacuum pump via a cooling trap cooled with dry ice-ethanol and a cooling trap cooled with liquid nitrogen, and low-boiling-point components were distilled into the cooling trap while stirring. This crude product was treated with 1 N HCl and then washed with water, and 33DFM-FHDAE (boiling point: 52° C./13.3 kPa) not containing tripropylamine was thereby obtained with a GC purity of 98.6%. The yield of the target product was 13.9 g, and the isolation yield was 65%.

$^1$H-NMR (CDCl$_3$): δ (ppm) 5.88, 5.92, 5.95, 6.01 (total 2H), 6.09 to 6.23 (1H)

$^{19}$F-NMR (CDCl$_3$): δ (ppm) −65.3 (2F), −74.3 (6F), −93.2 (1F), −105.8 (1F), −189.5 (1F)

Example 1-8

Synthesis of FHBAE

Tetraglyme (45.6 g) dehydrated with molecular sieve 4A, triethylamine (8.02 g, 79.2 mmol) and 3-buten-1-ol (4.28 g, 59.4 mmol) were charged in a nitrogen atmosphere into a 200 mL four-neck round bottom flask equipped with a reflux condenser, a dropping funnel and a thermometer and cooled in ice water while stirring with a stir bar until the internal temperature became 5° C. or lower. While keeping the internal temperature at 10° C. or lower, PFAS (15.2 g, 66.0 mmol) was added dropwise over 30 minutes. The internal temperature at the end of dropwise addition was 6° C. After ice was removed from the ice water bath 15 minutes after the completion of dropwise addition and the solution was stirred for 45 minutes, the internal temperature was 9° C. Subsequently, the reaction was allowed to proceed at room temperature overnight. As a result of GC analysis of the reaction solution, the conversion of PFAS was 100%.

The dropping funnel and the reflux condenser were removed, a water bath at room temperature was set to the four-neck flask and the flask was connected to a vacuum pump via a cooling trap cooled with dry ice-ethanol and a cooling trap cooled with liquid nitrogen, and low-boiling-point components were distilled into the cooling trap while stirring. After the water bath temperature was kept at room temperature (about 20° C.) for 1 hour, the water bath temperature was raised sequentially to 30° C., 40° C. and 50° C. and kept at each temperature for 30 minutes and at 60° C. for 2 hours. As a result, 10.9 g of FHBAE containing a small amount of triethylamine was obtained in the dry ice-ethanol cooling trap. This crude product was treated with 1 N HCl and then washed with water, and FHBAE not containing triethylamine was thereby obtained with a GC purity of 99.0%. The yield of the target product was 7.6 g, and the isolation yield was 64%.

$^1$H-NMR (CDCl$_3$): δ (ppm) 2.44 (2H), 4.02 (2H), 5.13 (2H), 5.79 (1H)

$^{19}$F-NMR (CDCl$_3$): δ (ppm) −73.9 (2F), −95.4 (2F), −107.4 (1F), −189.4 (1F)

Example 1-9

Synthesis of 44DFM-FHBAE

Tetraglyme (136.7 g) dehydrated with molecular sieve 4A, triethylamine (24.1 g, 238 mmol) and 1,1-bis(trifluoromethyl)-3-buten-1-ol (37.1 g, 178 mmol) were charged in a nitrogen atmosphere into a 500 mL four-neck round bottom flask equipped with a reflux condenser, a dropping funnel and a thermometer and cooled in ice water while stirring with a stir bar until the internal temperature became 5° C. or lower. While keeping the internal temperature at 10° C. or lower, PFAS (45.6 g, 198 mmol) was added dropwise over 1 hour. Ice was removed from the ice water bath 30 minutes after the completion of dropwise addition, and the solution was continuously stirred at room temperature overnight. As a result of GC analysis of the reaction solution, the conversion of PFAS was 100%.

The dropping funnel and the reflux condenser were removed, a water bath at room temperature was set to the four-neck flask and the flask was connected to a vacuum pump via a cooling trap cooled with dry ice-ethanol and a cooling trap cooled with liquid nitrogen, and low-boiling-point components were distilled into the cooling trap while stirring. The water bath temperature was kept at room temperature for 2 hours, then raised to 40° C., and kept for 2 hours. As a result, 60.1 g of 44DFM-FHBAE containing a small amount of triethylamine was obtained in the dry ice-ethanol cooling trap. This crude product was treated with 1 N HCl and then washed with 3.0 N brine. The lower layer was separated and collected, and 44DFM-FHBAE not containing triethylamine was thereby obtained with a GC purity of 97.9%. The yield of the target product was 53.7 g, and the isolation yield was 90%.

After distillation under reduced pressure, a target product having a purity of 99.5% or more was obtained in a distillation yield of 68%. The boiling point was 59° C./6.7 kPa.

$^1$H-NMR (CDCl$_3$): δ (ppm) 3.11 (2H), 5.30 (2H), 5.83 (1H)

$^{19}$F-NMR (CDCl$_3$): δ (ppm) −66.3 (2F), −73.8 (6F), −93.2 (1F), −105.5 (1F), −189.6 (1F)

Example 2-1

Synthesis of 2M-FHDAE Polymer

2M-FHDAE (6.00 g) was charged into a hastelloy-made autoclave having an internal volume of 120 mL. Isopropyl alcohol (0.93 g) that had been 10-fold diluted with HCFC-225cb was added, a solution obtained by 200-fold diluting IPP (48 mg) with HCFC-225cb was then added, and finally, HCFC-225cb was added to make the total amount of HCFC-225cb charged 53.02 g.

After repeating freeze-pump-thaw degassing twice using liquid nitrogen, the temperature was returned to about 0° C., and a nitrogen gas was introduced until reaching 0.3 MPaG (G indicates gauge pressure). The autoclave was set in a water bath and after stirring for 6 hours while keeping the internal temperature at 40° C., the autoclave was immersed in ice water and cooled to 20° C. or lower.

The reaction solution was moved from the autoclave to a beaker and combined with a washing solution using HCFC-225cb to make the total amount of contents 104 g and after stirring for 30 minutes, 126 g of n-hexane was added, followed by further stirring for 30 minutes. After filtration under reduced pressure, ethyl acetate was added to the obtained solid matter to make a total amount of 58 g. After stirring for 30 minutes, the polymer was coagulated by the addition of 126 g of n-hexane and filtered under reduced pressure. The same operation using ethyl acetate and n-hexane was repeated once more.

The resulting polymer was vacuum-dried overnight at 60° C. to obtain 4.72 g of a white polymer. The weight average molecular weight was 40,100, Td (3%) in air was 316° C., Td (3%) in nitrogen was 415° C., and Tg was 176° C.

From the analyses using $^1$H-, $^{13}$C- and $^{19}$F-NMRs and their two-dimensional NMRs, the obtained polymer was confirmed to be a homopolymer composed of a repeating unit shown below.

[Chem. 21]

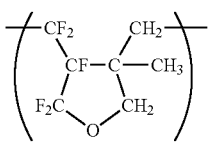

Examples 2-2 to 2-10

Syntheses 2 to 10 of 2M-FHDAE Polymer

Polymerization of 2M-FHDAE polymer was performed in the same manner as in Example 2-1 except that the preparation conditions in Example 2-1 were changed to the conditions shown in Table 1. The polymer yield, weight average molecular weight, thermal decomposition initiation temperature and glass transition temperature obtained are also shown in Table 1.

The polymer of Example 2-6 dissolved in all of tetrahydrofuran, ethyl acetate, acetone, dichloromethane and perfluorobenzene at a polymer concentration of 3 mass %.

(Measurement of Abbe's Number)

With respect to the above film of Example 2-6, the refractive indices at a wavelength of 486 nm, 589 nm and 656 nm were calculated using Metricon Fit attached to the device, and the Abbe's number was calculated according to the following formula (I). As a result, the Abbe's number was 57.26.

$$\nu_D = (n_D - 1)/(n_F - n_C) \quad (I)$$

$\nu_D$ is the Abbe's number, $n_D$ is the refractive index for light having a wavelength of 589 nm, $n_F$ is the refractive index for light having a wavelength of 486 nm, and $n_C$ is the refractive index for light having a wavelength of 656 nm.

Example 2-11

Synthesis (1) of Low-Molecular-Weight 2M-FHDAE Polymer

2M-FHDAE (3.00 g) was charged into a hastelloy-made autoclave having an internal volume of 120 mL. Isopropyl alcohol (3.73 g) was added, a solution obtained by 20-fold diluting 1PP (38 mg) with HCFC-225cb was then added, and finally, HCFC-225cb was added to make the total amount of

TABLE 1

| | | | | | Example | | | | | |
|---|---|---|---|---|---|---|---|---|---|---|
| | | 2-1 | 2-2 | 2-3 | 2-4 | 2-5 | 2-6 | 2-7 | 2-8 | 2-9 | 2-10 |
| Internal volume of reactor/cm³ | | 120 | 120 | 120 | 120 | 120 | 120 | 120 | 120 | 34 | 34 |
| 2M-FHDAE/g | | 6 | 6 | 6 | 6 | 6 | 6 | 6 | 6 | 5 | 5 |
| IPP/mg | | 48 | 24 | 24 | 24 | 24 | 24 | 24 | 24 | 60 | 20 |
| Molecular weight adjusting agent | Isopropyl alcohol/g | 0.93 | 0.93 | 0.47 | 0.23 | — | — | — | — | — | — |
| | Methanol/g | — | — | — | — | — | 0.93 | — | — | 0.093 | 0.31 |
| | n-Hexane/g | — | — | — | — | — | — | 0.93 | — | — | — |
| | Monoglyme/g | — | — | — | — | — | — | — | 0.93 | — | — |
| HCFC-225cb/g | | 53.02 | 53.04 | 53.51 | 53.74 | 53.98 | 53.04 | 53.04 | 53.04 | 14.85 | 14.67 |
| Reaction temperature/° C. | | 40 | 40 | 40 | 40 | 40 | 40 | 40 | 40 | 45 | 40 |
| Reaction time/hrs | | 6 | 6 | 6 | 6 | 6 | 6 | 6 | 6 | 6 | 3 |
| Polymer yield/g | | 4.72 | 3.27 | 4.41 | 5.05 | 5.6 | 5.05 | 3.86 | 4.64 | 4.69 | 3.49 |
| Weight average molecular weight | | 40,100 | 81,000 | 130,900 | 208,300 | 456,900 | 290,500 | 275,300 | 259,900 | 205,700 | 485,200 |
| Td(3%), in air/° C. | | 316 | 316 | 315 | 298 | 283 | 322 | 313 | 297 | 304 | 307 |
| Td(3%), in nitrogen/° C. | | 415 | 420 | 425 | 420 | 404 | 403 | 425 | 410 | 414 | not measured |
| Tg/° C. | | 176 | 186 | 186 | 187 | 163 | 184 | 187 | 169 | 183 | 182 |

(Measurement of Absorption Spectrum)

The polymer of Example 2-6 was dissolved at a concentration of 10 mass % in a mixed solvent of ethyl acetate and propylene glycol monomethyl ether acetate (in this order, mass ratio: 4:1). The solution was cast at room temperature using a PFA petri dish, left standing overnight, dried at 60° C. for 2 hours, then annealed at 220° C. for 30 minutes, and further hot-pressed at 220° C. to obtain a colorless transparent film with a smooth surface having a thickness of about 100 μm. The absorption spectrum of 200 to 1,700 nm was measured using UV-3100 manufactured by Shimadzu Corporation, as a result, absorption was not observed at 400 to 1,700 nm.

(Measurement of Refractive Index)

With respect to the above film of Example 2-6, the refractive indices of the film for light having a wavelength of 473 nm, 594 nm and 658 nm were measured using a refractometer (manufactured by U.S. Metricon, prism coupler: 2010/M), and the refractive index for light having a wavelength of 589 nm was calculated using Metricon Fit attached to the device. As a result, the refractive index was 1.41 (589 nm).

HCFC-225cb charged 52.89 g. Thereafter, polymerization and post-treatment were performed in the same manner as in Example 2-1 to obtain 1.44 g of a white polymer. The weight average molecular weight was 7,400, Td (3%) in air was 307° C., and Tg was 154° C.

Example 2-12

Synthesis of Low-Molecular-Weight 2M-FHDAE Polymer and End Stabilization (2)

2M-FHDAE (3.00 g) was charged into a hastelloy-made autoclave having an internal volume of 120 mL. $CF_3(CF_2)_3$-I (6.44 g) was added, a solution obtained by 200-fold diluting IPP (38 mg) with HCFC-225cb was then added, and finally, HCFC-225cb was added to make the total amount of HCFC-225cb charged 50.52 g. Thereafter, polymerization and post-treatment were performed in the same manner as in Example 2-1 to obtain 2.15 g of a white polymer. The weight average molecular weight was 12,200, Td (3%) in air was 296° C., and Tg was 157° C.

Next, the end group was stabilized as follows in accordance with the method described in International Publication WO2017/086465.

1.35 g of the obtained polymer was dissolved in HCFC-225cb (40.00 g) and charged into a hastelloy-made autoclave having an internal volume of 120 mL. Subsequently, a mixed solution of IPP (38 mg), HCFC-225cb (5.50 g) and n-hexane (0.675 g) was added, and HCFC-225cb was further added to make the total amount of the solution charged 67.50 g.

After repeating freeze-pump-thaw degassing twice using liquid nitrogen, the temperature was returned to about 0° C., and a nitrogen gas was introduced until reaching 0.3 MPaG. The autoclave was set in a water bath and after stirring for 7 hours while keeping the internal temperature at 70° C., the autoclave was allowed to cool.

The contents were moved to an eggplant flask together with a washing solution using HCFC225cb and concentrated on an evaporator until the weight of contents became 27.0 g. After coagulation by n-hexane and filtration, HCFC225cb was added to the obtained solid matter to make a total amount of 27 g, and the solid matter was dissolved with stirring. This operation of coagulation, filtration and dissolution was repeated and thereafter, the polymer was coagulated by n-hexane and vacuum-dried at 60° C. for 18 hours. The weight of the obtained white polymer was 1.22 g. When $^{19}$F-NMR was measured by dissolving the polymer in perfluorobenzene, peaks based on —CF2-I at −40 to −50 ppm of the polymer ends, which were observed before the treatment with IPP/n-hexane, disappeared.

Example 2-13

Synthesis of 2M-FHDAE Polymer

2M-FHDAE (6.00 g) was charged into a hastelloy-made autoclave having an internal volume of 120 mL. A solution obtained by 400-fold diluting IPP (24 mg) with ethyl acetate was then added, and finally, ethyl acetate was added to make the total amount of ethyl acetate charged 53.98 g.

After repeating freeze-pump-thaw degassing twice using liquid nitrogen, the temperature was returned to about 0° C., and a nitrogen gas was introduced until reaching 0.3 MPaG. The autoclave was set in a water bath and after stirring for 6 hours while keeping the internal temperature at 40° C., the autoclave was immersed in ice water and cooled to 20° C. or lower.

The reaction solution was moved from the autoclave to a beaker and combined with a washing solution of ethyl acetate to make the total amount of contents 70 g. After stirring for 30 minutes, 153 g of n-hexane was added, followed by further stirring for 30 minutes. After filtration under reduced pressure, ethyl acetate was added to the obtained solid matter to make a total amount of 70 g. After stirring for 30 minutes, the polymer was coagulated by the addition of 153 g of n-hexane and filtered under reduced pressure. The same operation using ethyl acetate and n-hexane was repeated once more.

The resulting polymer was vacuum-dried overnight at 60° C. to obtain 5.05 g of a white polymer. The weight average molecular weight was 62,200, Td (3%) in air was 304° C., Td (3%) in nitrogen was 386° C., and Tg was 188° C.

Example 2-14

Synthesis of FHDAE Polymer

FHDAE (3.00 g) was added to a 50 ml three-neck flask containing a stir bar, isopropyl alcohol (0.47 g) that had been 10-fold diluted with HCFC-225cb was added, a solution obtained by 100-fold diluting IPP (96 mg) with HCFC-225cb was then added, and finally, HCFC-225cb was added to make the total amount of HCFC-225cb charged 26.44 g.

After attaching a Dimroth condenser and repeating freeze-pump-thaw degassing twice using liquid nitrogen, the temperature was returned to about 0° C., and a nitrogen gas was introduced into the system. The contents were stirred for 6 hours by heating the system at 40° C. in a nitrogen-sealed state and after cooling in ice water, moved to a beaker. The total amount of the contents combined with a washing solution of HCFC-225cb was 52 g.

After stirring for 30 minutes, 63 g of n-hexane was added, and the contents were further stirred for 30 minutes. After filtration under reduced pressure, ethyl acetate was then added to make a total amount of 41 g followed by stirring for 30 minutes. 88 g of n-hexane was added, and stirring for 30 minutes and then filtration under reduced pressure were performed. The same operation using ethyl acetate and n-hexane was repeated once more.

The resulting polymer was vacuum-dried overnight at 60° C. to obtain 2.21 g of a white polymer. The thermal decomposition temperature Td (3%) in air of the obtained polymer was 301° C. This polymer dissolved in acetone at a concentration of 0.5 mass %.

The obtained polymer contains a repeating unit shown below.

[Chem. 22]

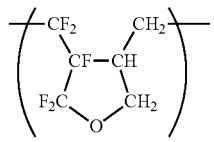

Example 2-15

Synthesis of 3M-FHDAE Polymer

3M-FHDAE (6.00 g) was charged into a hastelloy-made autoclave having an internal volume of 120 mL. A solution obtained by 100-fold diluting IPP (120 mg) with HCFC-225cb was added, and finally, HCFC-225cb was added to make the total amount of HCFC-225cb charged 53.88 g. Thereafter, polymerization was performed in the same manner as in Example 2-1 except that the polymerization temperature was changed to 45° C. The contents were moved to a beaker, and a washing solution of HCFC-225cb was added thereto. The total amount was 115 g. After stirring for 30 minutes, the polymer was coagulated by the addition of 172 g of methanol, stirred for 30 minutes, and filtered. The obtained polymer was dissolved in 93 g of HCFC-225cb, and the polymer was coagulated by 142 g of methanol and filtered. The same operation was repeated once more, and the polymer was vacuum-dried for 16 hours at 60° C. to obtain 5.17 g of a white polymer. The weight average molecular weight was 54,800, Td (3%) in air was 352° C., Td (3%) in nitrogen was 405° C., and Tg was 103° C.

The obtained polymer contains a repeating unit shown below.

[Chem. 23]

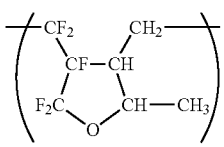

Example 2-16

Synthesis of 33DFM-FHDAE Polymer

33DFM-FHDAE (3.00 g) was charged into a hastelloy-made autoclave having an internal volume of 30 mL. A solution obtained by 40-fold diluting PFBPO (75 mg) with HCFC-225cb was added, and finally, HCFC-225cb was added to make the total amount of HCFC-225cb charged 11.93 g.

After repeating freeze-pump-thaw degassing twice using liquid nitrogen, the temperature was returned to about 0° C., and a nitrogen gas was introduced until reaching 0.3 MPaG. The autoclave was set in an oil bath and after stirring for 6 hours while keeping the internal temperature at 80° C., the autoclave was immersed in ice water and cooled to 20° C. or lower. The obtained reaction solution was a colorless transparent liquid.

The reaction solution was moved from the autoclave to a beaker, and 17.5 g of n-hexane was added while stirring, followed by further stirring for 30 minutes. After filtration under reduced pressure, HCFC-225cb was added to the obtained solid matter to make a total amount of 29 g. After stirring for 30 minutes, the polymer was coagulated by the addition of 38 g of n-hexane and filtered under reduced pressure. The same operation using HCFC-225cb and n-hexane was repeated once more.

The polymer was vacuum-dried for 32 hours at 60° C. to obtain 2.78 g of a white polymer. The weight average molecular weight was 20,300, Td (3%) in air was 389° C., and Tg was 119° C.

The obtained polymer contains a repeating unit shown below.

[Chem. 24]

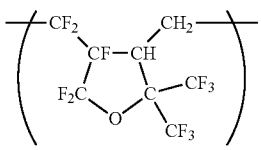

Example 2-17

Synthesis of FHBAE Polymer

FHBAE (6.00 g) was charged into a hastelloy-made autoclave having an internal volume of 120 mL. A solution obtained by 100-fold diluting IPP (120 mg) with HCFC-225cb was added, and finally, HCFC-225cb was added to make the total amount of HCFC-225cb charged 53.88 g. Thereafter, polymerization and post-treatment were performed in the same manner as in Example 2-1 except that the polymerization temperature was changed to 45° C. As a result, 2.4 g of a white polymer was obtained. The weight average molecular weight was 10,300, Td (3%) in air was 323° C., Td (3%) in nitrogen was 372° C., and Tg was 124° C. The obtained polymer dissolved in HCFC-225cb and acetone.

The obtained polymer contains a repeating unit shown below.

[Chem. 25]

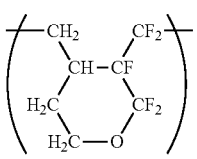

Example 2-18

Synthesis of 44DFM-FHBAE Polymer

44DFM-FHBAE (6.00 g) was charged into a hastelloy-made autoclave having an internal volume of 120 mL. A solution obtained by 400-fold diluting IPP (24 mg) with HCFC-225cb was added, and finally, HCFC-225cb was added to make the total amount of HCFC-225cb charged 53.98 g. Thereafter, polymerization and post-treatment were performed in the same manner as in Example 2-1 to obtain 5.01 g of a white polymer. The weight average molecular weight was 318,200, Td (3%) in air was 369° C., Td (3%) in nitrogen was 433° C., and Tg was 145.5° C. The obtained polymer dissolved in acetone, tetrahydrofuran and HCFC-225cb.

The obtained polymer contains a repeating unit shown below.

[Chem. 26]

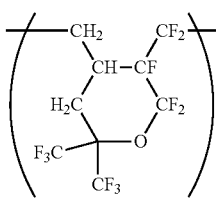

Example 2-19

Synthesis of Copolymer of FHDAE and 2M-FHDAE 2.30 g (12.2 mmol) of FHDAE and 3.70 g (18.3 mmol) of 2M-FHDAE were charged into a hastelloy-made autoclave having an internal volume of 120 mL. Isopropyl alcohol (0.466 g) that had been 20-fold diluted with HCFC-225cb was added, a solution obtained by 100-fold diluting IPP (24 mg) with HCFC-225cb was added, and finally, HCFC-225cb was added to make the total amount of HCFC-225cb charged 53.51 g. Thereafter, polymerization was performed in the same manner as in Example 2-1. The contents were moved to a beaker, and a washing solution of HCFC-225cb was added thereto. The total amount was 95 g. 20 g of ethyl acetate as a good solvent was added thereto, and the contents were stirred for 30 minutes. The polymer was coagulated by the addition of 139 g of n-hexane, stirred for 30 minutes, and filtered. After that, the obtained solid matter was dissolved in 39 g of ethyl acetate while stirring, and the polymer was coagulated by 86 g of n-hexane and filtered. The operation of dissolving in ethyl acetate and coagulating by n-hexane was repeated once more and after filtration, the polymer was vacuum-dried for 16 hours at 60° C. to obtain 3.38 g of a white polymer. The weight average molecular weight was 95,300, Td (3%) in air was 303° C., Td (3%) in nitrogen was 423° C., and Tg was 166° C.

The obtained polymer contains repeating units shown below.

[Chem. 27]

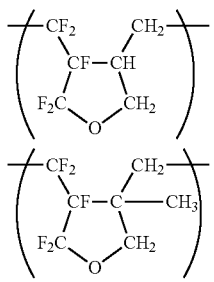

Example 2-20

Synthesis of Copolymer of 2M-FHDAE and C6FMA 4.85 g (24.0 mmol) of 2M-FHDAE and 1.15 g (2.67 mmol) of C6FMA were charged into a hastelloy-made autoclave having an internal volume of 120 mL. A solution obtained by 100-fold diluting IPP (120 mg) with HCFC-225cb was added, and finally, HCFC-225cb was added to make the total amount of HCFC-225cb charged 53.88 g. Thereafter, polymerization was performed in the same manner as in Example 2-1. The contents were moved to a beaker, and a washing solution of HCFC-225cb was added thereto. The total amount was 108 g. After stirring for 30 minutes, the polymer was coagulated by the addition of 166 g of methanol, stirred for 30 minutes, and filtered. The obtained polymer was dissolved in 43 g of HCFC-225cb, and the polymer was coagulated by 66 g of methanol and filtered. The same operation was repeated once more, and the polymer was then vacuum-dried for 16 hours at room temperature to obtain 0.78 g of a white polymer. The weight average molecular weight was 21,200, Td (3%) in air was 267° C., Td (3%) in nitrogen was 292° C., and Tg was 66° C. $^{19}$F-NMR was measured by dissolving the polymer in perfluorobenzene. As a result, the ratio of 2M-FHDAE and C6FMA repeating units was 57:43.

The obtained polymer contains repeating units shown below.

[Chem. 28]

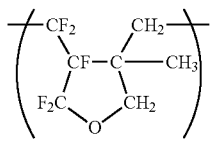

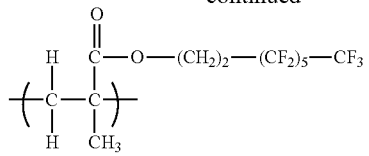

Example 2-21

Synthesis of Copolymer of 2M-FHDAE and (Perfluorohexyl)ethylene 2.21 g (10.9 mmol) of 2M-FHDAE and 3.79 g (10.9 mmol) of (perfluorohexyl)ethylene were charged into a hastelloy-made autoclave having an internal volume of 120 mL. A solution obtained by 100-fold diluting IPP (120 mg) with HCFC-225cb was added, and finally, HCFC-225cb was added to make the total amount of HCFC-225cb charged 53.88 g. Thereafter, polymerization was performed in the same manner as in Example 2-1 except that the polymerization temperature was changed to 45° C. The contents were moved to a beaker, and a washing solution of HCFC-225cb was added thereto. The total amount was 108 g. After stirring for 30 minutes, the polymer was coagulated by the addition of 134 g of n-hexane, stirred for 30 minutes, and filtered. The obtained polymer was dissolved in 68 g of HCFC-225cb, and the polymer was coagulated by 88 g of n-hexane and filtered. The same operation was repeated once more, and the polymer was then vacuum-dried for 24 hours at 60° C. to obtain 1.84 g of a white polymer. Td (3%) in air was 289° C., Td (3%) in nitrogen was 387° C., and Tg was 142° C. $^{19}$F-NMR was measured by dissolving the polymer in perfluorobenzene. As a result, the ratio of 2M-FHDAE and (perfluorohexyl)ethylene repeating units was 84:16.

The obtained polymer contains repeating units shown below.

[Chem. 29]

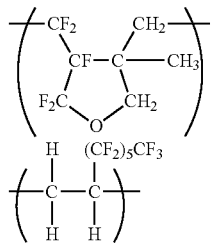

While the invention has been described in detail and with reference to specific embodiments thereof, it will be apparent to one skilled in the art that various changes and modifications can be made therein without departing from the spirit and scope thereof. This application is based on a Japanese patent application filed on Dec. 26, 2017 (Application No. 2017-249732), the contents of which are incorporated herein by reference.

INDUSTRIAL APPLICABILITY

In the present invention, a novel fluorine-containing diene compound is provided, and a novel fluorine-containing polymer obtained from a fluorine-containing compound such as the fluorine-containing diene compound as a raw material monomer is expected to be utilized in a wide variety of fields such as optical material, electronic material, etc.

The invention claimed is:

1. A fluorine-containing diene compound represented by the following formula I:

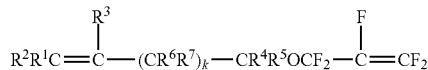

wherein in the formula, each of $R^1$ to $R^3$, $R^6$, and $R^7$ is independently a hydrogen atom, a chlorine atom, a fluorine atom, or an alkyl group having a carbon number of 1 to 5 which may be substituted by a fluorine atom, each of $R^4$ and $R^5$ is independently a hydrogen atom, a chloride atom, or an alkyl group having a carbon number of 1 to 5 which may be substituted by a fluorine atom, k is 0 or 1, and at least one of $R^1$ to $R^7$ is a hydrogen atom.

2. The fluorine-containing diene compound according to claim 1, wherein in the formula I, each of $R^1$ and $R^2$ is independently a hydrogen atom or a fluorine atom, $R^3$ is a hydrogen atom, a chlorine atom, a fluorine atom, a methyl group, or a trifluoromethyl group, and each of $R^4$ and $R^5$ is independently a hydrogen atom, a methyl group, or a trifluoromethyl group.

3. A method for producing a fluorine-containing diene compound represented by the following formula I, the method comprising reacting a compound represented by the following formula a with a compound represented by the following formula b in the presence of a base:

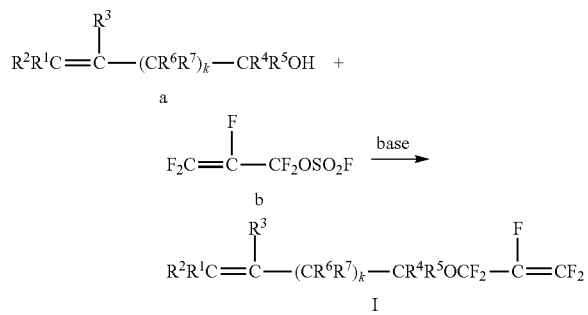

wherein in the formulae, each of $R^1$ to $R^7$ is independently a hydrogen atom, a chlorine atom, a fluorine atom, or an alkyl group having a carbon number of 1 to 5 which may be substituted by a fluorine atom, k is 0 or 1, and at least one of $R^1$ to $R^7$ is a hydrogen atom.

4. The method for producing a fluorine-containing diene compound according to claim 3, wherein the reaction is performed in the presence of a solvent.

5. The method for producing a fluorine-containing diene compound according to claim 3, wherein the base is an aliphatic tertiary amine.

6. The method for producing a fluorine-containing diene compound according to claim 4, wherein the solvent contains at least one of glyme and nitrile.

7. A fluorine-containing polymer obtained by polymerizing a fluorine-containing compound represented by the following formula I' as a raw material monomer:

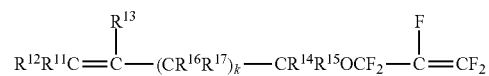

wherein in the formula, each of $R^{11}$ to $R^{13}$, $R^{16}$, and $R^{17}$ is independently a hydrogen atom, a chlorine atom, a fluorine atom, or a monovalent organic group which may have a heteroatom, each of $R^{14}$ and $E^{15}$ is independently a hydrogen atom, a chlorine atom, or a monovalent organic group which may have a heteroatom, k is 0 or 1, at least one of $R^{11}$ to $R^{17}$ is a hydrogen atom, $R^{11}$ or $R^{12}$ may combine with any one of $R^{13}$ to $R^{17}$ to form a ring, and $R^{13}$ may combine with any one of $R^{11}$, $R^{12}$ and $R^{14}$ to $R^{17}$ to form a ring.

8. The fluorine-containing polymer according to claim 7, wherein the fluorine-containing compound represented by the formula I' is a fluorine-containing diene compound represented by the following formula I:

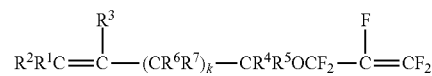

wherein in the formula, each of $R^1$ to $R^3$, $R^6$, and $R^7$ is independently a hydrogen atom, a chlorine atom, a fluorine atom, or an alkyl group having a carbon number of 1 to 5 which may be substituted by a fluorine atom, each of $R^4$ and $R^5$ is independently a hydrogen atom, a chlorine atom, or an alkyl group having a carbon number of 1 to 5 which may be substituted by a fluorine atom, k is 0 or 1, and at least one of $R^1$ to $R^7$ is a hydrogen atom.

9. The fluorine-containing polymer according to claim 8, wherein in formula I, each of $R^1$ and $R^2$ is independently a hydrogen atom or a fluorine atom, $R^3$ is a hydrogen atom, a chlorine atom, a fluorine atom, a methyl group, or a trifluoromethyl group, and each of $R^4$ and $R^5$ is independently a hydrogen atom, a methyl group, or a trifluoromethyl group.

10. A method for producing a fluorine-containing polymer, the method comprising polymerizing a raw material monomer containing a fluorine-containing compound represented by the following formula I':

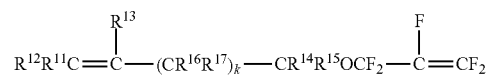

wherein in the formula, each of $R^{11}$ to $R^{13}$, $R^{16}$, and $R^{17}$ is independently a hydrogen atom, a chlorine atom, a fluorine atom, or a monovalent organic group which may have a heteroatom, each of $R^{14}$ and $R^{12}$ is independently a hydrogen atom, a chloride atom, or a monovalent organic group which may have a heteroatom, k is 0 or 1, at least one of $R^{11}$ to $R^{17}$ is a hydrogen atom, $R^{11}$ or $R^{12}$ may combine with any one of $R^{13}$ to $R^{17}$ to form a ring, and $R^{13}$ may combine with any one of $R^{11}$, $R^{12}$ and $R^{14}$ to $R^{17}$ to form a ring.

11. The method for producing a fluorine-containing polymer according to claim 10, wherein the fluorine-containing compound represented by formula I' is a fluorine-containing diene compound represented by the following formula I:

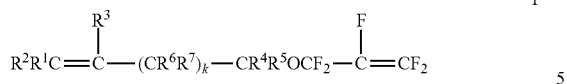

wherein in the formula, each of $R^1$ to $R^3$, $R^6$, and $R^7$ is independently a hydrogen atom, a chlorine atom, a fluorine atom, or an alkyl group having a carbon number of 1 to 5 which may be substituted by a fluorine atom, each of $R^4$ and $R^5$ is independently a hydrogen atom, a chlorine atom, or an alkyl group having a carbon number of 1 to 5 which may be substituted by a fluorine atom, k is 0 or 1, and at least one of $R^1$ to $R^7$ is a hydrogen atom.

12. The method for producing a fluorine-containing polymer according to claim 11, wherein in formula I, each of $R^1$ and $R^2$ is independently a hydrogen atom or a fluorine atom, $R^3$ is a hydrogen atom, a chlorine atom, a fluorine atom, a methyl group, or a trifluoromethyl group, and each of $R^4$ and $R^5$ is independently a hydrogen atom, a methyl group, or a trifluoromethyl group.

\* \* \* \* \*